(12) United States Patent
Devenney et al.

(10) Patent No.: US 6,802,991 B2
(45) Date of Patent: Oct. 12, 2004

(54) METHOD FOR PREPARING A CSX PHOSTIMULABLE PHOSPHOR AND PHOSPHOR SCREENS THEREFROM

(75) Inventors: Martin Devenney, Mountain View, CA (US); Casper Reaves, Los Angeles, CA (US); Paul Leblans, Kontich (BE); Luc Struye, Mortsel (BE)

(73) Assignees: Symyx Technologies, Inc., Santa Clara, CA (US); AGFA-Gevaert, N.V., Mortsel (BE)

( * ) Notice: Subject to any disclaimer, the term of this patent is extended or adjusted under 35 U.S.C. 154(b) by 0 days.

(21) Appl. No.: 10/032,308

(22) Filed: Dec. 21, 2001

(65) Prior Publication Data

US 2004/0140453 A1 Jul. 22, 2004

Related U.S. Application Data

(63) Continuation of application No. PCT/US00/16904, filed on Jun. 19, 2000.
(60) Provisional application No. 60/159,004, filed on Oct. 8, 1999, and provisional application No. 60/142,276, filed on Jul. 2, 1999.

(51) Int. Cl.[7] .......................... C09K 11/61; C09K 11/55
(52) U.S. Cl. ......................... 252/301.4 H; 204/192.26; 427/69; 427/70; 427/157; 427/226; 427/255.39; 427/64
(58) Field of Search .................... 427/69, 70, 64, 427/255.39, 157, 226; 252/301.4 H; 204/192.26

(56) References Cited

U.S. PATENT DOCUMENTS

| | | |
|---|---|---|
| 2,502,529 A | 4/1950 | Murray |
| 2,887,379 A | 5/1959 | Blake et al. |
| 3,300,310 A | 1/1967 | Kennard et al. |
| 3,300,311 A | 1/1967 | Kennard et al. |
| 3,617,285 A | 11/1971 | Staudenmayer ................. 96/82 |
| 3,743,833 A | 7/1973 | Martic et al. ................ 250/483 |
| 3,859,527 A | 1/1975 | Luckey ........................ 250/327 |
| 4,780,376 A | 10/1988 | Nakamura ................... 428/691 |
| 4,879,202 A | 11/1989 | Hosoi et al. ................. 430/139 |
| 4,947,046 A | 8/1990 | Kawabata et al. ........ 250/484.1 |
| 5,028,509 A | 7/1991 | Shimada et al. ............. 430/139 |
| 5,055,681 A | 10/1991 | Tsuchino et al. ......... 250/327.2 |

(List continued on next page.)

FOREIGN PATENT DOCUMENTS

| | | |
|---|---|---|
| EP | 0 174 875 | 3/1986 |
| EP | 0 185 534 | 6/1986 |
| EP | 0 252 991 | 1/1988 |
| WO | WO 01/03156 | 1/2001 |

OTHER PUBLICATIONS

Pedero et al, "Analysis of Optical Behaviour of Eu2+ Ions in CsCl Crystals", Physica Status Solidi B, Oct. 1, 1997, vol. 203, No. 2, pp. 591–598.*

Pedrero N.E. et al. "Analysis of the Optical Bahaviour of $Eu^{2+}$ Ions in CsCl Crystals" Physica Status Solidi, B, Oct. 1, 1997, Akademie Verlag, Germany, vol. 203, No. 2, pp. 591–598.

*Primary Examiner*—C. Melissa Koslow
(74) *Attorney, Agent, or Firm*—Sennniger, Powers, Leavitt & Roedel (57) ABSTRACT

A CsX:Eu phosphor produced by heating a cesium halide with a Europium compound containing one or more halides selected from the group consisting of F, Cl, Br and I. Preferably the Europium compound is selected from the group consisting of $EuX'_2$, and $EuX'_3$ and EuX', X' being one or more halides selected from the group consisting of F, Cl, Br and I. The invention also includes novel phosphors having properties inherent to the manufacturing process as well as other phosphors containing a mixture of Br and Cl in the cesium halide, europium doped phosphor.

A method for preparing a binderless phosphor screen using these phosphors and a method for recording and reproducing an X-ray image using such screens are also disclosed.

33 Claims, 4 Drawing Sheets

U.S. PATENT DOCUMENTS

| | | | |
|---|---|---|---|
| 5,736,069 A | 4/1998 | Willems et al. | 252/301.4 H |
| 6,479,835 B1 * | 11/2002 | Struye et al. | 250/584 |
| 6,495,850 B1 | 12/2002 | Struye et al. | |
| 6,501,088 B1 | 12/2002 | Struye et al. | |
| 6,512,240 B1 | 1/2003 | Leblans et al. | |
| 6,528,812 B1 | 3/2003 | Leblans et al. | |
| 2001/0007352 A1 * | 7/2001 | Hell et al. | 250/484.4 |

* cited by examiner

METHOD FOR PREPARING A CSX PHOTOSTIMULABLE PHOSPHOR AND PHOSPHOR SCREENS THEREFROM

This application is a continuation of PCT/US00/16904 filed Jun. 19, 2000, which was published in English pursuant to PCT Article 21(2) as International Publication No. WO 01/03156 A1 on Jan. 11, 2001 and which itself claims the benefit of U.S. Provisional Application No. 601142,276 filed Jul. 2, 1999 and U.S. Provisional Application No. 60/159, 004 filed Oct. 8, 1999, all of which are incorporated herein by reference.

BACKGROUND OF THE INVENTION

1. Field of the Invention

The present invention relates to a method for recording and reproducing images of objects made by high energy radiation. It relates especially to a method for manufacturing a cesium halide storage phosphor, particular phosphors and a storage phosphor panel containing them.

2. Discussion

A well-known use of phosphors is in the production of X-ray images. In a conventional radiographic system an X-ray radiograph is obtained by X-rays transmitted image-wise through an object and converted into light of corresponding intensity in a so-called intensifying screen (X-ray conversion screen) wherein phosphor particles absorb the transmitted X-rays and convert them into visible light and/or ultraviolet radiation to which a photographic film is more sensitive than to the direct impact of X-rays.

According to another method of recording and reproducing an X-ray pattern disclosed e.g., in U.S. Pat. No. 3,859, 527 a special type of phosphor is used, known as a photo-stimulable phosphor, which being incorporated in a panel, is exposed to incident pattern-wise modulated X-ray beam and as a result thereof temporarily stores energy contained in the X-ray radiation pattern. At some interval after the exposure, a beam of visible or infra-red light scans the panel to stimulate the release of stored energy as light that is detected and converted to sequential electrical signals which are can be processed to produce a visible image. For this purpose, the phosphor should store as much as possible of the incident X-ray energy and emit as little as possible of the stored energy until stimulated by the scanning beam. This is called "digital radiography" or "computed radiography".

The image quality that is produced by a conventional as well as by a digital radiographic system depends largely on the construction of the phosphor screen. Generally, the thinner a phosphor screen at a given amount of absorption of X-rays, the better the image quality will be. This means that the lower the ratio of binder to phosphor of a phosphor screen, the better the image quality, attainable with that screen, will be. Optimum sharpness can thus to be obtained when screens without any binder, are used. Such screens can be produced, e.g., by physical vapor deposition, which may be thermal vapor deposition, sputtering, electron beam deposition or other of phosphor material on a substrate. However, this production method can not be used to produce high quality screens with every arbitrary phosphor available. The mentioned production method leads to the best results when phosphor crystals with high crystal symmetry and simple chemical composition are used. Phosphors having complicated crystal structures as, e.g., alkaline earth fluorohalides, tend to decompose (partially) under physical vapor deposition and the production of screens in this way while using phosphors with complicated crystal structure is quasi impossible and leads to sub-optimal results. The use of alkali metal halide phosphors in storage screens or panels is well known in the art of storage phosphor radiology and the high crystal symmetry of these phosphors makes it possible to provide structured screens and binderless screens. In e.g., U.S. Pat. No. 5,055,681 a storage phosphor screen comprising an alkali metal phosphor in a pile-like structure is disclosed.

In U.S. Pat. No. 5,736,069 an alkali metal storage phosphor is disclosed corresponding to the formula:

wherein: $M^{1+}$ is at least one member selected from the group consisting of Li, Na, K, Cs and Rb, $M^{2+}$ is at least one member selected from the group consisting of Be, Mg, Ca, Sr, Ba, Zn, Cd, Cu, Pb and Ni, $M^{3+}$ is at least one member selected from the group consisting of Sc, Y, La, Ce, Pr, Nd, Pm, Sm, Eu, Gd, Tb, Dy, Ho, Er, Tm, Yb, Lu, Al, Bi, In and Ga, Z is at least one member selected from the group $Ga^{1+}$, $Ge^{2+}$, $Sn^{2+}$, $Sb^{3+}$ and $As^{3+}$, X, X' and X" can be the same or different and each represents a halogen atom selected from the group consisting of F, Br, Cl, and I, and $0 \leq a \leq 1$, $0 \leq b \leq 1$ and $0 \leq c \leq 0.2$.

In EP-A-174 875 and EP-B-252 991 (and U.S. Pat. No. 5,028,509), amongst other alkali metal stimulable phosphors a CsBr:Eu phosphor is disclosed, wherein the Eu is incorporated in the CsBr by firing CsBr with Europium oxide.

The alkali metal phosphors according to the disclosures mentioned above find applications for preparing structured screens and binderless screens, it would, nonetheless, be advantageous to have CsX phosphor with enhanced speed.

SUMMARY OF THE INVENTION

It is a first object of the invention to provide a method for producing a novel cesium halide phosphor, where such phosphor exhibits a high speed and thus provides more degrees of freedom for producing storage phosphor panels that combine high speed with high resolution.

It is a second object of the invention to provide a panel, containing cesium halide phosphor that exhibits a high speed combined with a high resolution.

It is a third object of the invention to provide a method for recording and reproducing images of objects made by high energy radiation.

Further objects and advantages of the invention will become clear from the detailed description hereinafter. All references cited are incorporated by reference.

The object of the invention is realized by providing a method for manufacturing a CsX:Eu stimulable phosphor, wherein X represents a halide selected from the group consisting of Br, Cl and combinations thereof comprising the steps of:

mixing or otherwise combining the CsX with between $10^{-3}$ mol % and 5 mol % of a Europium compound, relative to the moles of CsX, the Europium compound being selected from the group consisting of $EuX'_2$, $EuX'_3$ and $EuOX'$, X' being one or more halide selected from the group consisting of F, Cl, Br and I;

heating (e.g., firing) said mixture at a temperature above about 450° C.; and cooling said mixture. Typically, the resulting CsX:Eu phosphor is recovered from the crucible or other suitable container in which it was prepared. The CsX:Eu phosphor resulting from such methods is novel, and provides substantial practical advantages over known CsX:Eu phosphors.

The second object of the invention is realized by manufacturing a phosphor screen containing a CsX:Eu stimulable phosphor, wherein X represents a halide selected from the group consisting of Br, Cl and combinations thereof comprising the steps of:

preparing said CsX:Eu phosphor by heating (e.g., firing) a mixture of said CsX with between $10^{-3}$ mol % and 5 mol % of an Europium compound selected from the group consisting of $EuX'_2$, $EuX'_3$ and EuOX', X' being one or more halide selected from the group consisting of F, Cl, Br and I; and applying said phosphor on a substrate by a method selected from the group consisting of chemical vapor deposition or physical vapor deposition, including thermal vapor deposition, electron beam evaporation, magnetron sputtering, radio frequency sputtering and pulsed laser deposition or atomization techniques such as spray drying, thermal spraying, etc.

The second object of the invention is also realized by manufacturing a phosphor screen containing a CsX:Eu stimulable phosphor, wherein X represents a halide selected from the group consisting of Br, Cl and combinations thereof comprising the steps of:

bringing multiple containers of said CsX and an Europium compound selected from the group consisting of $EuX'_2$, $EuX'_3$ and EuOX', X' being one or more halide selected from the group consisting of F, Cl, Br and I in condition for vapor deposition; and depositing, by a method selected from the group consisting of chemical vapor deposition or physical vapor deposition, including thermal vapor deposition, electron beam evaporation, magnetron sputtering, radio frequency sputtering and pulsed laser deposition or atomization techniques such as spray drying, thermal spraying, etc, both said CsX and said Europium compound on a substrate in such a ratio that on said substrate a CsX phosphor, doped with between $10^{-3}$ mol % and 5 mol % of an Europium compound, is formed.

The third object of the invention is realized by providing a method for recording and reproducing images of objects made by high energy radiation comprising the steps of:

exposing a panel containing a CsX:Eu stimulable phosphor, wherein X represents a halide selected from the group consisting of Br, Cl and combinations thereof, including between $10^{-3}$ mol % and 5 mol % of a Europium dopant, said dopant originating from a Europium compound selected from the group consisting of $EuX'_2$, $EuX'_3$ and EuOX', X' being one or more halide selected from the group consisting of F, Cl, Br and I, with X-ray radiation for storing energy in said phosphor, stimulating said panel with stimulating radiation having a wavelength between 500 nm and 1100 nm, releasing said stored energy as stimulated radiation and collecting said stimulated radiation.

DETAILED DESCRIPTION

In this document the term "X-ray" has to be understood as any penetrating radiation and includes irradiation originating from a radioisotope (e.g. Co60, Ir192, Se75, etc.), radiation created by an X-ray generator of any type, radiation and high energy particles created by a high energy radiation generator (e.g. Betatron), and/or radiation from a sample labeled with a radioisotope as is the case of, e.g., autoradiography.

Conventional wisdom in the art of producing stimulable phosphors teaches that when doping a phosphor, e.g. BaFBr, with Eu-ions, it does not matter under what form the Eu-ions are mixed with the raw mix before firing. It is accepted that oxides of trivalent and divalent europium can be used as well as halides of trivalent and divalent europium and that the same phosphor quality will be obtained.

Also in EP-A-174 875 there is no teaching that in the manufacturing of alkali metal halide phosphors the use of different Europium compounds for doping the alkali metal halide would give phosphors with different quality or enhanced qualities (e.g., enhanced properties). When studying the examples of EP-A-174 875 it seems that only $Eu_2O_3$ is a suitable compound for doping a simple CsBr phosphor.

It was now surprisingly found that a CsX:Eu phosphor could be produced in the manner disclosed herein, and that such phosphor exhibits much higher speed than the prior art CsX:Eu phosphor. The CsX:Eu phosphor of the present invention is prepared by using as an Eu dopant in the raw mix a Europium compound selected from the group consisting of $EuX'_2$, $EuX'_3$ and EuOX', where X' is one or more halide selected from the group consisting of F, Cl, Br and I. Especially the use of $EuBr_3$, $EuBr_2$, $EuCl_2$ and EuOBr gave very good results. This result was even more surprising when consideration is given to the observation that when doping a CsBr phosphor with Tl, better performance was achieved using $Tl_2O$ instead of TlBr.

The Europium compound selected from the group consisting of $EuX'_2$, $EuX'_3$ and EuOX', X' being one or more halide selected from the group consisting of F, Cl, Br and I, is preferably mixed with the CsX in such a way that between $10^{-3}$ mol % and 5 mol % of the Europium compound is present, relative to the number of moles of CsX. Preferably said Europium compound is mixed with the CsX in such a way that between $10^{-1}$ mol % and 3 mol % of the Europium compound is present relative to the CsX. These starting materials are combined and/or intimately mixed by suitable methods known in the art.

The combined starting materials are preferably heated (e.g., fired) at a temperature ranging from about 450° C. to about 1000° C., more preferably at a temperature ranging from about 550° C. to about 1000° C., and still more preferably at a temperature ranging from about 650° C. to about 1000° C. and most preferably at a temperature of about 700° C. The dwell time at the firing temperature is not critical, and can range from about 1 minute to about 10 hours, from about 5 minutes to about 6 hours or from about 5 minutes to about 1 hour. The combined starting materials are most preferably heated to a temperature (e.g., fired at temperatures) above the melting point of CsBr. The heated mixture can be cooled by methods known in the art. Cooling rates can be typical of those employed in the art and can vary based on the method of cooling.

In addition the phosphors of the present invention include a mixture of halides in the formula CsX:Eu, where X is a mixture of Br and Cl. This results in a phosphor of the formula $CsBr_aCl_b$:Eu where a+b=1, a and b are each numbers and a ranges from about 0.99 to about 0.8 and b ranges from about 0.01 to about 0.2. Preferably, a ranges from about 0.99 to about 0.95 and b ranges from about 0.01 to about 0.05. Also, a may range from about 0.95 to about 0.8 or from about 0.9 to about 0.8; also, b may range from about 0.05 to about 0.2 or from about 0.1 to about 0.2. These phosphors may be prepared by the vapor deposition methods discussed herein by starting with targets of CsBr, CsCl and $EuCl_2$ and controlling the deposition.

The phosphors prepared by the aforementioned methods exhibit substantially improved speed. Moreover, all samples of CsBr:Eu prepared with europium halides in the raw mixtures exhibited a blue photoluminescence (254 nm excitation) after firing with a power in Watt that is at least 100 times higher than the energy of a very weak red photoluminescence. Samples prepared with $Eu_2O_3$ as the starting material exhibited blue and red photoluminescence (254 nm excitation) after firing, wherein the power of the blue photoluminescence is substantially less than 100 times the energy of the red photoluminescence.

The phosphor produced by the methods described herein can beneficially be used in a powder panel wherein the phosphor is applied to a support from a solution containing a binder resin and the phosphor. Phosphor screens comprising a layer containing a phosphor embedded in a binder resin are well known in the art. In this case any binder known in the art can be used to form a screen or panel comprising a CsBr:Eu or $CsBr_aCl_b$:Eu phosphor according to the present invention. Suitable binders are, e.g., gelatin, polysaccharides such as dextrin, gum Arabic, and synthetic polymers such as polyvinyl butyl, polyvinyl acetate, nitrocellulose, ethylcellulose, vinylidene chloride-vinyl chloride copolymer, polyalkyl (meth)acrylate, vinyl chloride-vinyl acetate copolymer, polyurethane, cellulose acetate, cellulose acetate butyrate, polyvinyl alcohol, polystyrene, polyester, etc. These and other useful binders are disclosed e.g. in U.S. Pat. Nos. 2,502,529, 2,887,379, 3,617,285, 3,300,310, 3,300,311 and 3,743,833. A mixture of two or more of these binders may be used, e.g., a mixture of polyethyl acrylate and cellulose acetobutyrate.

The weight ratio of phosphor to binder is generally within the range of from 50:50 to 99:1, preferably from 80:20 to 99:1. Preferably a self-supporting or supported layer of phosphor particles according to the present invention comprises said particles dispersed in a binding medium and a protective coating thereover characterized in that the binding medium substantially consists of one or more hydrogenated styrene-diene block copolymers, having a saturated rubber block, as rubbery and/or elastomeric polymers. The polymer can be represented by the formula A-B-A (tri-block) or by the formula A-B (di-block), wherein A represents styrene and B represents the hydrogenated diene block, e.g., ethylene-butylene or ethylene-propylene. Further the ratio by volume of phosphor to binding medium is preferably more than 70/30 and still more preferably more than 85/15.

The phosphor is especially well suited for manufacturing a "binderless" storage phosphor panel by physical vapor deposition comprising the deposition so as to have a "binderless" phosphor screen. Although any method for depositing a phosphor without a binder can be used to apply the cesium halide phosphor made by the method of this invention (e.g., CsX:Eu or $CsBr_aCl_b$:Eu) to a support, it is preferred to use a method selected from the group consisting of chemical vapor deposition or physical vapor deposition, including thermal vapor deposition, electron beam evaporation, magnetron sputtering, radio frequency sputtering and pulsed laser deposition or atomization techniques such as spray drying, thermal spraying, etc. Most preferably thermal vapor deposition is used to prepare binderless screens containing a phosphor of this invention. The deposition of the phosphor according to this invention is preferably so that the CsX:Eu stimulable phosphor is present in the form of columnar crystals. Such panels have been disclosed in, e.g., EP-A-185 534, U.S. Pat. No. 4,947,046, JP-A-61 245099, etc. In order to deposit a phosphor of this invention on a substrate by thermal vapor deposition, this phosphor is brought in to a heatable vessel. This vessel and the substrate are brought in a deposition chamber that can be evacuated to at least $10^{-4}$ mbar. By adjusting the temperature of the vessel containing the phosphor and the evaporation time the thickness of the phosphor layer on the substrate can be adjusted.

A "binderless" storage phosphor panel containing a cesium halide phosphor can also be manufactured depositing simultaneously CsX and $EuX'_2$, $EuX'_3$ and/or EuOX', X being a combination of Br and Cl in any ratio and X' being one or more halides. Thus the invention encompasses a method for manufacturing a phosphor screen containing a CsX:Eu stimulable phosphor, wherein X represents a halide selected from the group consisting of Br and Cl comprising the steps of:

bringing multiple containers of said CsX and an Europium compound selected from the group consisting of $EuX'_2$, $EuX'_3$ and EuOX', X' being one or more halide selected from the group consisting of F, Cl, Br and I in condition for vapor deposition and depositing, by a method selected from the group consisting of chemical vapor deposition or physical vapor deposition, including thermal evaporation, electron beam evaporation, magnetron sputtering, radio frequency sputtering and pulsed laser deposition or atomization techniques such as spray drying, thermal spraying, etc, both said CsX and said Europium compound on a substrate in such a ratio that on said substrate a CsX phosphor, doped with between $10^{-3}$ mol % and 5 mol % of Europium, is formed.

The deposition can proceed from a single container containing a mixture of the starting compounds in the desired proportions. Thus the method encompasses further a method for manufacturing a phosphor screen containing a CsX:Eu stimulable phosphor, wherein X represents one or more halides selected from the group consisting of Br and Cl comprising the steps of:

mixing said CsX with between $10^{-3}$ and 5 mol % of an Europium compound selected from the group consisting of $EuX'_2$, $EuX'_3$ and EuOX', X' being one or more halide selected from the group consisting of F, Cl, Br and I bringing said mixture in condition for vapor deposition and depositing said mixture on a substrate by a method selected from the group consisting of chemical vapor deposition or physical vapor deposition, including thermal vapor deposition, electron beam evaporation, magnetron sputtering, radio frequency sputtering and pulsed laser deposition or atomization techniques such as spray drying, thermal spraying, etc.

Bringing in condition for thermal vapor deposition means that the ingredients are brought in heatable containers and that these containers are placed, together with the substrate on which the phosphor has to be deposited in a deposition chamber that can be evacuated to at least $10^{-4}$ mbar. Generally, there are at least three possible embodiments: the starting ingredients are mixed into a single heatable container, the starting ingredients are separated into individual heatable containers and the pre-formed CsX:Eu phosphor is placed into one or more heatable containers.

Support materials for storage screens, binderless as well as binder containing screens, containing a phosphor in accordance with the present invention, include cardboard, plastic films such as films of cellulose acetate, polyvinyl chloride, polyvinyl acetate, polyacrylonitrile, polystyrene, polyester, polyethylene terephthalate, polyamide, polyimide, cellulose triacetate and polycarbonate; metal sheets such as aluminum foil and aluminum alloy foil; ordinary papers; baryta paper; resin-coated papers; pigment papers containing titanium dioxide or the like; papers sized with polyvinyl alcohol or the like; and glass sheets. A plastic film is preferably employed as the support material for a binder containing screen; a glass or Al sheet is preferably employed as the support material for a binderless screen.

The plastic film may contain a light-absorbing material such as carbon black, or may contain a light-reflecting material such as titanium dioxide or barium sulfate. The former is appropriate for preparing a high-resolution type storage screen, while the latter is appropriate for preparing a high-sensitivity type storage screen.

Examples of preferred supports include polyethylene terephthalate, clear or blue colored or black colored (e.g., LUMIRROR C, type X30, (trade name) supplied by Toray Industries, Tokyo, Japan), polyethylene terephthalate filled with $TiO_2$ or with $BaSO_4$. Metals such as e.g. aluminum, bismuth and the like may be deposited e.g. by vaporization techniques to get a polyester support having radiation-reflective properties.

These supports may have a thickness which may differ depending on the material of the support, and may generally be between 60 and 1000 mm, more preferably between 80 and 500 mm from the standpoint of handling.

EXAMPLES

MEASUREMENTS OF THE PROPERTIES OF THE PHOSPHORS

The determination of the properties of the doped CsX crystals according to the present invention proceeded through following measurements:

In a first measurement the "prompt" emission spectrum of the phosphor under X-ray excitation was measured. The measurement proceeds with a multichannel detector under excitation by X-ray irradiation and was carried out with an X-ray source operating at room temperature at 80 kVp and 15 mA. Under continuous X-ray excitation light of different wavelengths were produced. The rays of emission light, having different wavelengths, were collected and amplified in the different channels of the multichannel detector.

In a second measurement the stimulation spectrum was determined. The light of a tungsten (quartz-iodine) lamp was fed into a monochromator (SPEX 270M trade name of Yvon-Jobin, France) and then mechanically chopped with a rotating wheel with a single slit. The lamp provides a continuous spectrum extending from the near UV through the visible spectrum into the infrared. The 520.24.33.0 grating from Yvon-Jobin was a 1200 line/mm grating covering the visible range from 350 nm to 1100 nm in the first order and was blazed at 750 nm. The wavelength of the stimulating light can be set via a step motor connected to the monochromator under the control of a computer. The second harmonic of the monochromator was eliminated by placing a 4 mm Schott GG435 filter in front of the phosphor screen, when the monochromator is set at a wavelength longer than 800 nm a RG 665 SCHOTT filter (trade name) was added. By chopping the stimulating light (duty cycle 1/200) only a small fraction of the absorbed energy in the phosphor was released. Only the AC signal was measured to eliminate the offset caused due to e.g. the dark current of the photomultiplier. A good signal to noise ratio was obtained by averaging several pulses. Upon completing the measurement the computer corrects the curve for the intensity wavelength dependence of the tungsten lamp and the diffraction efficiency of the grating In the third measurement the total photostimulable energy stored upon exposure to a given X-ray dose was determined. This property is expressed as "conversion efficiency" (C.E.):

Prior to X-ray excitation any residual energy still present in the phosphor screen was removed by irradiation with light of a 500 W quartz-halogen lamp. The phosphor screen was then excited with an X-ray source operating at 80 kVp and 5 mA. For that purpose the BALTEAUGRAPHE 2000 (tradename) X-ray source of Balteau, France was used. The low energy X-rays are filtered out with a 21 mm thick aluminum plate to harden the X-ray spectrum. After X-ray excitation the phosphor screen was transferred in the dark to the measurement set-up. In this setup laser light was used to photostimulate the X-ray irradiated phosphor screen. The laser used in this measurement was a diode laser emitting at 690 nm with a power of 5 mW. The diode laser was the type LT030-MD, trade name of Sharp, USA.

The laser-optics comprise an electronic shutter, a beam-expander and a filter. A photomultiplier (HAMAMATSU R 376) collects the light emitted by the photostimulation and gives a corresponding electrical current. The measurement procedure was controlled by a Hewlett Packard HP 382 (tradename) computer connected to a HP 6944 (tradename) multiprogrammer. After amplification with a current to voltage converter a TEKTRONIX TDS 420 (tradename) digital oscilloscope visualizes the photocurrent obtained. When the electronic shutter was opened the laser beam begins to stimulate the phosphor screen and the digital oscilloscope was triggered. Using a diaphragm placed in contact with the screen the light emitted by only 7 $mm^2$ was collected. Approximately half of the laser power (2 mW) reaches the screen surface. In this way the intensity of the stimulating beam was more uniform.

The stimulating laser light (transmitted by the crystal) and the stimulated emission light are separated by a 6 mm BG 39 SCHOTT (trade name) filter, so that only the emitted light reaches the photomultiplier.

The signal amplitude from the photomultiplier is linear with the intensity of the photostimulating light and with the stored photostimulable energy. The signal decreases with time. When the signal curve was entered the oscilloscope was triggered a second time to measure the offset which was defined as the component of error that was constant and independent of inputs. After subtracting this offset the point at which the signal reaches 1/e of the maximum value was calculated. The integral below the curve was then calculated from the start to this 1/e point. The function was described mathematically by $f(t)=A.e^{-t/\tau}$; wherein A is the amplitude, t is the time constant, $\tau$ is stimulation time, and e is the base number of natural logarithms.

The 1/e point is reached when $t=\tau$ at which 63% of the stored energy has been released. To obtain said result, the computer multiplies the integral with the sensitivity of the system. The sensitivity of the photomultiplier and amplifier have therefore to be measured as a function of anode-cathode voltage of the photomultiplier and the convolution of the emission spectrum of the phosphor, the transmission spectrum of the 6 mm BG 39 SCHOTT (trade name) filter and the wavelength dependence of the response of the photomultiplier have to be calculated. Because the emission light is scattered in all directions only a fraction of the emitted light is detected by the photomultiplier. The position of the panel and photomultiplier are such that 10% of the total emission was, detected by the photomultiplier. After all these corrections have been made a conversion efficiency value (C.E.) was obtained in $pJ/mm^2/mR$.

PREPARATION OF THE PROSPHORS

Basically all phosphors were prepared in the same way and only the nature and the amount of the activator (dopant) and the nature of the carrier gas were changed. The comparative CsBr:Eu phosphors were prepared by adding $Eu_2O_3$ to the CsBr before firing and the invention CsBr:Eu phosphors were prepared by adding either $EuCl_2$ or $EuBr_3$ to the CsBr before firing. Also CsBr:Tl phosphors were prepared wherein the dopant was either $Tl_2O$ or one of TlBr or $TlCl_3.4H_2O$. All chemicals were used as received from commercial suppliers, except for $EuBr_3$ and EuOBr. $EuBr_3$ was received in hydrated form from a commercial vendor and dried before preparing the CsBr:Eu phosphors of the present invention. Specifically, hydrated europium bromide was placed in a desicator with desiccant and dried under vacuum for 24 hours. Despite such drying, it is possible that residual water was present and that the europium bromide was in a partially hydrated form. Moreover, given the hygroscopic nature of the materials involved, water may also become included in the europium bromide, in other starting materials and/or in the combined mixture during transfer and handling of such compounds or mixtures. The synthesis of EuOBr is described below.

Crystals of activated CsBr were prepared by mixing by manual grinding 20 g of 99.999% pure CsBr with the activator compound in the right proportion (see Table 1, below). The mixture was placed in an $Al_2O_3$ crucible and placed in the quartz tube of a tube furnace.

The quartz tube was sealed with a flange with water lock and flushed with carrier gas prior to firing and during the firing process. The gas flow rate was 120 cc/min. The carrier gas was either nitrogen or, alternatively, Ar (with 5.8 mol % $H_2$), and is indicated in Table 1, below for particular examples.

The furnace temperature was increased from room temperature to 43° C. at a rate of 5° C./min. Dwell time at this temperature was 6 hours. Next, the temperature was ramped to 700° C. at 10° C./min. Dwell time at 700° C. was 5 min. The furnace was cooled to room temperature at 10° C./min.

The crucible containing the phosphor was removed from the furnace and the crucible was broken to set the phosphor crystals free. Larger crystalline particles were selected and polished to a thickness of ca. 500 μm for measurement.

In the following Table 1 the starting materials for the synthesis of the comparative phosphors and invention phosphors are given, as well as their conversion efficiency (CE). Preparation of EuOBr:

7.0 g (0.02 mol) of $Eu_2O_3$ was slowly added to a reactor containing 50 ml of deionised water and 22.4 g (0.13 mol) of a 47% HBr solution. Next, 3.9 g (0.004 mol) of $NH_4Br$ was added. The solution was heated to 60° C. and stirred until a clear, colourless solution was obtained.

Next, the solution was evaporated to dryness. To this aim, it was poured in a quartz container and placed in a sealed quartz tube. Before heating, the quartz tube was flushed with pure $N_2$ for 15 minutes.

For drying under $N_2$ flow the following temperature programme was used:

starting temperature: 120° C.,
dwell time at 120° C.: 3 hours,
rise-time from 120 to 300° C.: 2 hours,
dwell time at 300° C.: 12 hours,
rise-time from 300 to 480° C.: 15 minutes,
dwell time at 480° C.: 2 hours.

After drying, the tube was allowed to cool for 1 hour. The resulting powder was slightly yellowish and showed the characteristic $Eu^{2+}$ emission under 254 nm excitation. Nevertheless, XRD analysis, the Eu/Br ratio determined via ICP-OES and ionchromatography, showed that the resulting product was almost pure EuOBr.

Comparative Example Phosphors:

The comparative example phosphors were prepared by adding $EU_2O_3$ to CsBr. Crystals of activated CsBr were prepared by mixing by manual grinding ca. 20 g of 99.999% pure CsBr with the activator compound in the right proportion. The mixture was placed in an $Al_2O_3$ crucible and placed in the quartz tube of a tube furnace. The quartz tube was sealed with a flange with oil lock and flushed with the 5.8 mol % $H_2$ in Ar carrier gas prior to firing and during the firing process. The gas flow rate was 120 cc/min. The furnace temperature was increased from room temperature to 43° C. at a rate of 5° C./min. Dwell time at this temperature was 6 hours. Next, the temperature was ramped to 700° C. at 10° C./min. Dwell time at 700° C. was 5 min. The furnace was cooled to room temperature at 10° C./min. The crucible containing the phosphor was removed from the furnace, cooled and the phosphor crystals were taken from the crucible. Larger crystalline particles were selected and polished to a thickness of ca. 500 μm for measurement.

The conversion efficiency of the reference BaF(Br,I):Eu phosphor was measured under stimulation with a He-Ne laser and using a BG-3 (6 mm) filter to separate the emission end stimulation light.

TABLE 1

| Sample NR. | Dopant | Concentration of Eu vs. Cs (mol %) | Phosphor composition | Carrier gas | C.E. pJ/mm²/ mR |
|---|---|---|---|---|---|
| Reference | | | BaF(Br,I):Eu | | 57 |
| Comp. Example 1 | $Eu_2O_3$ | $10^{-3}$ | CsBr:Eu | $Ar/H_2$ | 2.1 |
| Comp. Example 2 | $Eu_2O_3$ | $10^{-2}$ | CSBr:Eu | $Ar/H_2$ | 5 |
| Comp. Example 3 | $Eu_2O_3$ | $10^{-1}$ | CsBr:Eu | $Ar/H_2$ | 1.9 |
| Comp. Example 4 | $Eu_2O_3$ | $3.10^{-1}$ | CsBr:Eu | $Ar/H_2$ | 1.4 |
| Comp. Example 5 | $Eu_2O_3$ | 1 | CSBr:Eu | $Ar/H_2$ | 12 |
| Comp. Example 6 | $Eu_2O_3$ | 3 | CSCl:Eu | $Ar/H_2$ | 11 |
| Example 7 | $EuCl_2$ | $10^{-3}$ | CsBr:Eu | $Ar/H_2$ | 2.1 |
| Example 8 | $EuCl_2$ | $10^{-2}$ | CsBr:Eu | $Ar/H_2$ | 13 |
| Example 9 | $EuCl_2$ | $10^{-1}$ | CsBr:Eu | $Ar/H_2$ | 27 |
| Example 10 | $EuCl_2$ | $3.10^{-}$ | CsBr:Eu | $Ar/H_2$ | 56 |
| Example 11 | $EuCl_2$ | 1 | CsBr:Eu | $Ar/H_2$ | 101 |
| Example 12 | $EuCl_2$ | 3 | CsBr:Eu | $Ar/H_2$ | 37 |
| Example 13 | $EuCl_2$ | $10^{-3}$ | CsBr:Eu | $N_2$ | 4.6 |
| Example 14 | $EuCl_2$ | $10^{-2}$ | CsBr:Eu | $N_2$ | 15 |

TABLE 1-continued

| Sample NR. | Dopant | Concentration of Eu vs. Cs (mol %) | Phosphor composition | Carrier gas | C.E. pJ/mm$^2$/mR |
|---|---|---|---|---|---|
| Example 15 | EuCl$_2$ | $3.10^{-1}$ | CsBr:Eu | N$_2$ | 110 |
| Example 16 | EuBr$_3$ | $10^{-3}$ | CsBr:Eu | Ar/H$_2$ | 4.6 |
| Example 17 | EuBr$_3$ | $10^{-2}$ | CsBr:Eu | Ar/H$_2$ | 22 |
| Example 18 | EuBr$_3$ | $10^{-1}$ | CsBr:Eu | Ar/H$_2$ | 23.4 |
| Example 19 | EuBr$_3$ | $3.10^{-1}$ | CsBr:Eu | Ar/H$_2$ | 137 |
| Example 20 | EuBr$_3$ | 1 | CsBr:Eu | Ar/H$_2$ | 124 |
| Example 21 | EuBr$_3$ | 3 | CsBr:Eu | Ar/H$_2$ | 53 |
| Comp. Example 22 | Tl$_2$O$_3$ | $3.10^{-1}$ | CsBr:Tl | Ar/H$_2$ | 0.077 |
| Comp. Example 23 | TlCl$_3$ | $3.10^{-1}$ | CsBr:Tl | Ar/H$_2$ | 0 |
| Comp. Example 24 | TlBr$_3$ | $3.10^-$ | CsBr:Tl | Ar/H$_2$ | 0 |
| Comp. Example 25 | Tl$_2$O$_3$ | $3.10^{-1}$ | CsBr:Tl | N$_2$ | 0.154 |
| Example 26 | EuOBr | $10^{-2}$ | CsBr:Eu | Ar/H$_2$ | 30 |

Example 27

Figure 1:
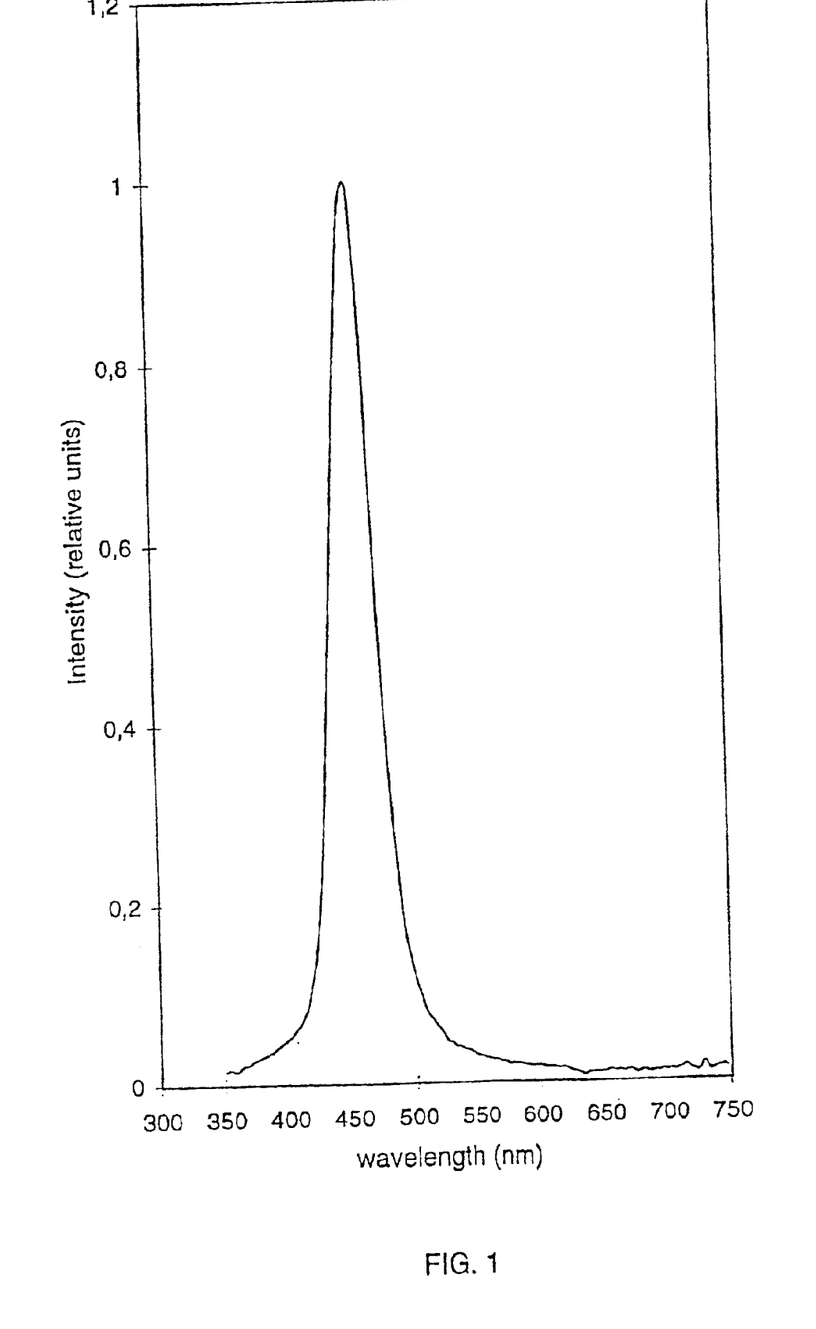
FIG. 1 shows the emission spectrum of an invention CsBr:Eu phosphor.
Figure 2:
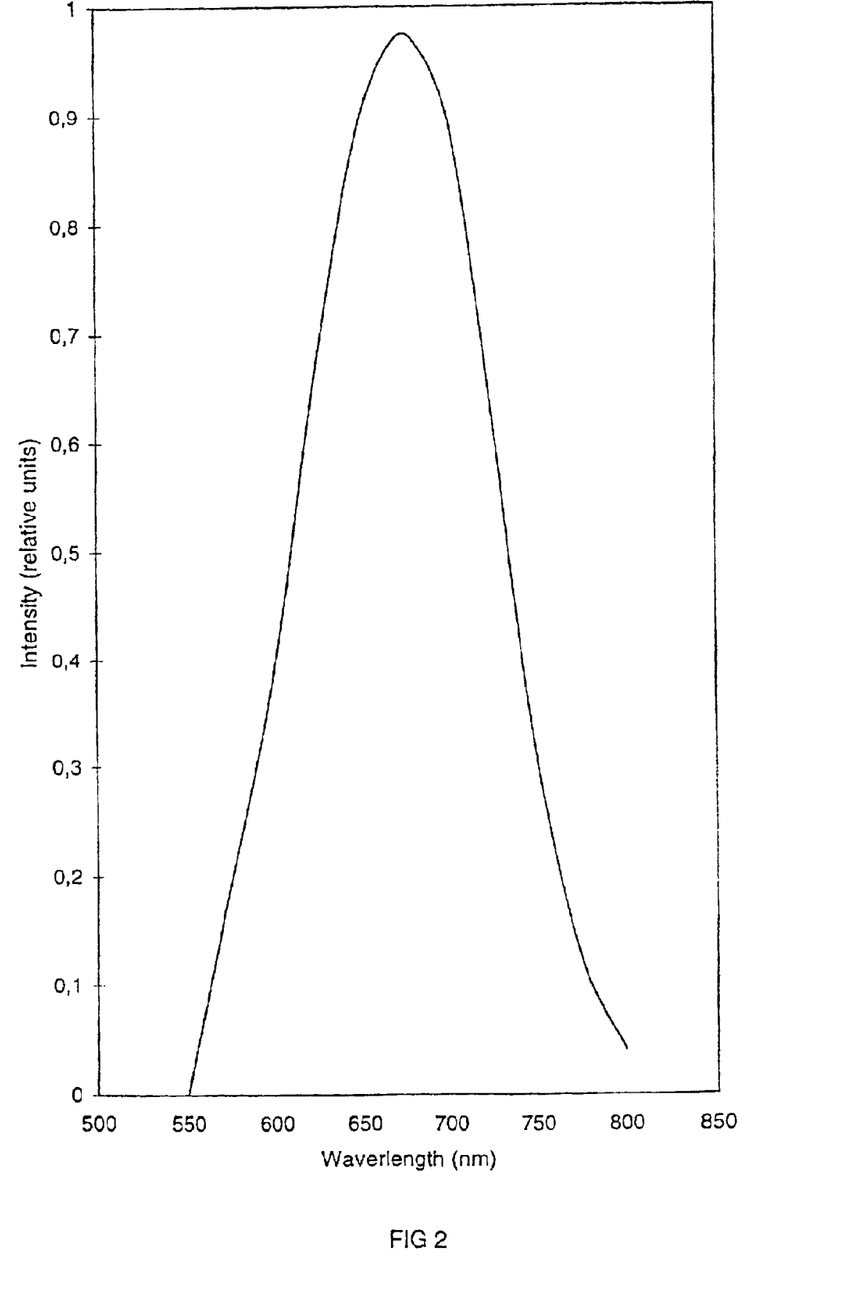
FIG. 2 shows the stimulation spectrum of an invention CsBr:Eu phosphor.
Figure 3:
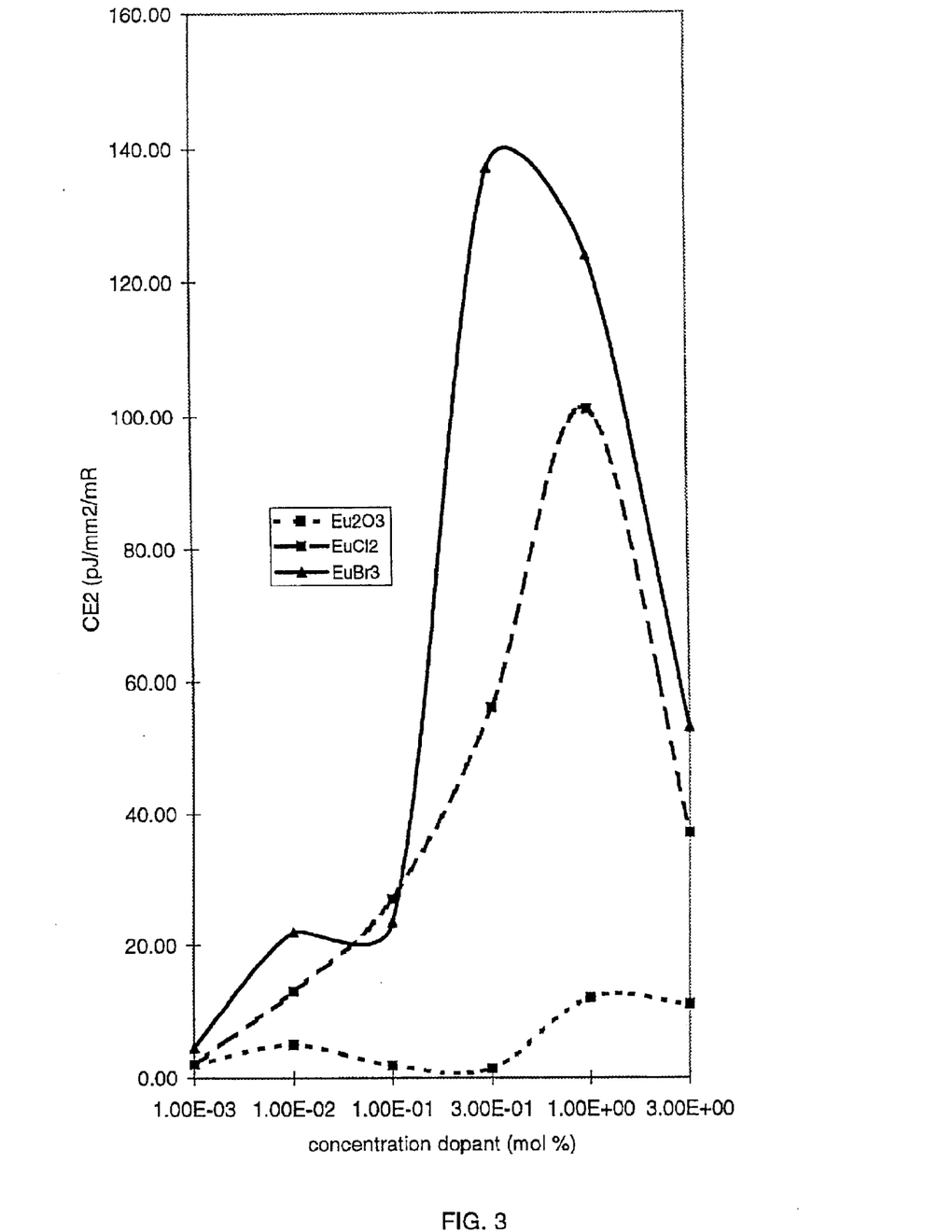
FIG. 3 shows the conversion efficiency of the CsBr:Eu phosphors as a function of the concentration and the type of dopant.
Figure 4:
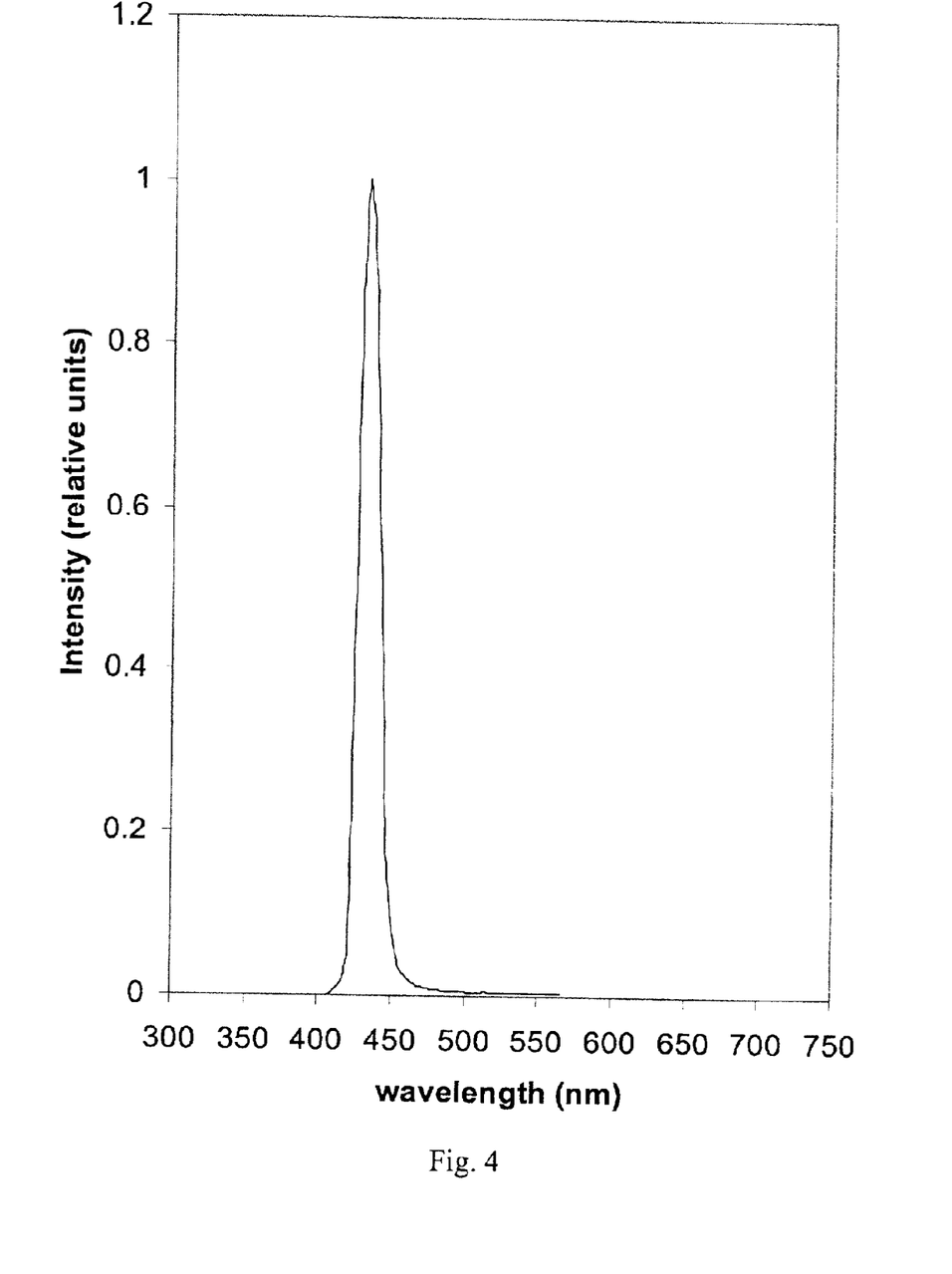
FIG. 4 shows the ultra-violet excited (280 nm) luminescence spectrum recorded from a film of europium doped cesium bromide.

A film of cesium bromide doped with europium chloride was deposited simultaneously on quartz and silicon substrates. The substrate for deposition consisted of a three-inch quartz wafer. A three-inch diameter semicircular silicon substrate was attached to one half of the quartz wafer. Phosphors CsBr:EuCl$_2$ ([Eu]=1 mol % vs Cs) were prepared as described for example 11. The film of cesium bromide doped with europium was prepared by the thermal evaporation of the phosphor samples in a deposition chamber operating at a pressure of approximately $8 \times 10^{-6}$ mbar. Chunks of the bulk phosphor were loaded into three separate evaporation crucibles (alumina) in the chamber. After evacuation of the chamber, the three crucibles were simultaneously heated to 550° C. Deposition was initiated on the substrates facing the crucibles by opening a flag placed between the crucibles and the substrate. The orientation of the evaporation crucibles with respect to the substrate was such that a film of even thickness was deposited over the predefined substrate area. The deposition rate from each crucible was approximately 60 Å/sec and was monitored using quartz crystal monitors. The distance between the substrate and the evaporation crucibles was 15 inches. The quartz and silicon substrates were subsequently removed from the chamber and a protective layer of aluminum oxide (1000 Å) deposited over the film on the substrates using r.f. magnetron sputtering. The final thickness of the film was approximately 30 μm as measured by profilometry. Blue emission was observed from the film by illuminating the sample with ultraviolet light (254 nm). The photoluminescence spectrum is shown in FIG. 4. Conversion Efficiency= 19.3 pJ/mm$^2$/mR.

The luminescence spectrum was measured from the europium doped cesium bromide film on the silicon substrate using Spex (TRADENAME) double monochromators for the photoexcitation wavelength (280 nm) and to disperse the resulting luminescence which was detected by a spectrally corrected photomultiplier.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles, patents and references, including patent applications and publications, are incorporated herein by reference for all purposes.

What is claimed is:

1. A method for producing a CsX:Eu stimulable phosphor, wherein X represents Br, or a combination of Br and Cl, comprising the steps of:
    mixing CsX with an Europium compound selected from the group consisting of EuX'$_2$, EuX'$_3$ and EuOX', X' being selected from the group consisting of F, Cl, Br, I and combinations thereof,
    heating said mixture at a temperature above 450° C.,
    cooling said mixture, and
    optionally recovering the CsX:Eu phosphor.

2. A method according to claim 1, wherein between $10^{-3}$ and 5 mol % of said Europium compound is mixed with said CsX.

3. A method according to claim 1, wherein between $10^{-3}$ and 3 mol % of said Europium compound is mixed with said CsX.

4. A method according to claim 1, wherein X' is a member selected from the group consisting of Cl and Br.

5. A method according to claim 2, wherein X' is a member selected from the group consisting of Cl and Br.

6. A method according to claim 3, wherein X'is a member selected from the group consisting of Cl and Br.

7. A binderless phosphor screen containing a CsX:Eu phosphor prepared according to claim 1.

8. A binderless phosphor screen containing a CsX:Eu phosphor prepared according to claim 2.

9. A binderless phosphor screen containing a CsX:Eu phosphor prepared according to claim 3.

10. A binderless phosphor screen containing a CsX:Eu phosphor prepared according to claim 4.

11. A binderless phosphor screen containing a CsX:Eu phosphor prepared according to claim 5.

12. A binderless phosphor screen containing a CsX:Eu phosphor prepared according to claim 6.

13. A method for producing a binderless phosphor screen comprising the steps of
    producing a CsX:Eu phosphor with the method of claim 1 and
    depositing said phosphor on a substrate by a method selected from the group consisting of physical vapor deposition, chemical vapor deposition or an atomization technique.

14. A method for manufacturing a binderless phosphor screen on a substrate containing a CsX:Eu stimulable phosphor, wherein X represents a halide selected from the group consisting of Br, Cl and combinations thereof comprising the steps of:
    bringing heatable multiple containers of CsX and an Europium compound selected from the group consisting of EuX'$_2$, EuX'$_3$ and EuOX', X' being selected from the group consisting of F, Cl, Br, I and combinations thereof, together with the substrate; and
    depositing, by a method selected from the group consisting of physical vapor deposition, chemical vapor deposition or atomization technique, both said CsX and said Europium compound on a substrate in such a ratio that on said substrate a CsX phosphor, doped with between $10^{-3}$ and 5 mol % of Europium, is formed.

15. A method for manufacturing a phosphor screen containing a CsX:Eu stimulable phosphor, wherein X represents a halide selected from the group consisting of Br and Cl comprising the steps of:

mixing CsX with between $10^{-3}$ and 5 mol % of an Europium compound selected from the group consisting of EuX'$_2$, EuX'$_3$ and EuOX', X' being selected from the group consisting of F, Cl, Br, I and combinations thereof, bringing said mixture in a container together with a substrate, and depositing said mixture on the substrate by a method selected from the group consisting of physical vapor deposition, chemical vapor deposition or atomization technique.

16. A method for recording and reproducing images of objects made by high energy radiation comprising:

exposing a panel with X-ray radiation, said panel comprising a CsX:Eu stimulable phosphor, wherein X represents a halide selected from the group consisting of Br, Cl and combinations thereof, including between $10^{-3}$ and 5 mol % of an Europium dopant, said dopant originating from an Europium compound selected from the group consisting of EuX'$_2$ and EuX'$_3$ and EuOX', X' being selected from the group consisting of F, Cl, Br, I and combinations thereof, stimulating said panel with radiation having a wavelength between 500 nm and 1100 nm thereby releasing stimulated radiation and collecting said stimulated radiation.

17. A phosphor of the formula CsBr$_a$Cl$_b$:Eu where a+b=1, and a ranges from about 0.99 to about 0.8 and b ranges from about 0.01 to about 0.2.

18. The phosphor of claim 17, wherein a ranges from about 0.99 to about 0.95 and b ranges from about 0.01 to about 0.05.

19. A CsX:Eu compound prepared according to one of the methods of claims 1, 2, 3, 4, 5 or 6.

20. A phosphor characterized by the formula CsX:Eu, wherein X is selected from the group consisting of Br, Cl and combinations thereof and said phosphor exhibiting, when excited with radiation of 254 nm, a blue photoluminescence and a red photoluminescence wherein said blue photoluminescence has a power (Watt) at least 100 times higher than said red photoluminescence.

21. The phosphor of claim 20, wherein X is Br.

22. A binderless phosphor screen comprising a CsX:Eu stimulable phosphor according to claim 20.

23. A binderless phosphor screen comprising a CsX:Eu stimulable phosphor, according to claim 21.

24. A method for producing a CsX:Eu stimulable phosphor, wherein X represents a halide selected from the group consisting of Br, Cl and combinations thereof, comprising the steps of:

mixing CsX with between $10^{-3}$ and 5 mol % of an Europium compound selected from the group consisting of EuX'$_2$, EuX'$_3$ and EuOX', X' being selected from the group consisting of F, Cl, Br, I and combinations thereof, heating said mixture at a temperature above 450° C., cooling said mixture, and optionally recovering the CsX:Eu phosphor.

25. The method of claim 24 wherein X' is a member selected from the group consisting of Br and Cl.

26. The method of claim 24 wherein between $10^{-1}$ and 3 mol % of said Europium compound is mixed with said CsX.

27. The method of claim 26 wherein X' is a member selected from the group consisting of Br and Cl.

28. A binderless phosphor screen containing a CsX:Eu phosphor prepared according to the method of claim 24.

29. A binderless phosphor screen containing a CsX:Eu phosphor prepared according to the method of claim 25.

30. A binderless phosphor screen containing a CsX:Eu phosphor prepared according to the method of claim 26.

31. A binderless phosphor screen containing a CsX:Eu phosphor prepared according to the method of claim 27.

32. A method for producing a binderless phosphor screen comprising the steps of:

producing a CsX:Eu phosphor according to the method of claim 24, and depositing said phosphor on a substrate by a method selected from the group consisting of physical vapor deposition, chemical vapor deposition or an atomization technique.

33. A CsX:Eu compound prepared according to claim 24.

* * * * *

UNITED STATES PATENT AND TRADEMARK OFFICE
CERTIFICATE OF CORRECTION

PATENT NO. : 6,802,991 B2
DATED : October 12, 2004
INVENTOR(S) : Devenney et al.

It is certified that error appears in the above-identified patent and that said Letters Patent is hereby corrected as shown below:

<u>Column 12,</u>
Line 19, delete "$10^{-3}$" and insert -- $10^{-1}$ --
Line 25, please add a space between "X'" and "is"

Signed and Sealed this

Twenty-second Day of March, 2005

JON W. DUDAS
*Director of the United States Patent and Trademark Office*